United States Patent
Du-Thumm et al.

(10) Patent No.: US 7,354,569 B2
(45) Date of Patent: Apr. 8, 2008

(54) CHEWABLE ANTIPLAQUE CONFECTIONERY DENTAL COMPOSITION

(75) Inventors: Laurence Du-Thumm, Plainsboro, NJ (US); Lori H. Szeles, Howell, NJ (US); Richard J. Sullivan, Somerset, NJ (US); James G. Masters, Ringoes, NJ (US); Richard S. Robinson, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 371 days.

(21) Appl. No.: 10/618,331

(22) Filed: Jul. 11, 2003

(65) Prior Publication Data

US 2005/0008582 A1 Jan. 13, 2005

(51) Int. Cl.
*A61K 9/68* (2006.01)

(52) U.S. Cl. ............... 424/48; 426/3; 426/5; 426/6; 514/835

(58) Field of Classification Search ............. None
See application file for complete search history.

(56) References Cited

U.S. PATENT DOCUMENTS

| | | | |
|---|---|---|---|
| 2,323,102 A * | 6/1943 | Staples ............... 426/3 |
| 3,235,460 A | 2/1966 | Ennever |
| 4,148,872 A * | 4/1979 | Wagenknecht et al. ....... 424/48 |
| 4,178,362 A | 12/1979 | Hoogendoorn et al. |
| 4,238,475 A * | 12/1980 | Witzel et al. ............. 424/48 |
| 4,353,891 A | 10/1982 | Guggenheim et al. |
| 4,981,698 A * | 1/1991 | Cherukuri et al. ........... 426/5 |
| 4,992,420 A | 2/1991 | Neeser |
| 5,236,720 A * | 8/1993 | Cherukuri ............. 426/3 |
| 5,320,830 A | 6/1994 | Lukacovich et al. |
| 5,487,902 A * | 1/1996 | Andersen et al. ........... 426/3 |
| 5,747,005 A | 5/1998 | Barels et al. |
| 6,180,143 B1 * | 1/2001 | Rapp et al. ............. 426/3 |
| 6,379,654 B1 * | 4/2002 | Gebreselassie et al. ....... 424/50 |
| 2002/0006385 A1 | 1/2002 | Tsuchiya |
| 2005/0175733 A1 * | 8/2005 | Thorengaard et al. ........ 426/3 |

FOREIGN PATENT DOCUMENTS

| | | |
|---|---|---|
| ES | 2 131 006 | 7/1999 |
| GB | 824680 | 12/1959 |
| GB | 1 294 767 | 11/1972 |
| JP | 63104908 | 5/1988 |
| JP | 02250816 | 10/1990 |
| JP | 04173056 | 6/1992 |

* cited by examiner

*Primary Examiner*—Frederick Krass
(74) *Attorney, Agent, or Firm*—Ellen K Park

(57) ABSTRACT

A chewable confectionery dental composition delivering to the mouth a unit dose of a plaque reducing enzyme the composition comprising an enzyme and a non-cariogenic sweetener, the enzyme being incorporated in the composition at a temperature less than about 80° C.

28 Claims, No Drawings

CHEWABLE ANTIPLAQUE CONFECTIONERY DENTAL COMPOSITION

BACKGROUND OF THE INVENTION

1. Field of the Invention

The present invention relates to a chewable confectionery composition which reduces the presence of dental plaque from the chewing surfaces of teeth and more particularly the invention relates to a chewable confectionery composition which contains a small but effective amount of a an enzyme effective to disrupt or interfere with plaque formation and adhesion to tooth surfaces.

2. The Prior Art

Oral compositions such as toothpastes, gels and mouth washes are designed to loosen and remove plaque in conjunction with a regular toothbrushing regimen. Dental plaque is present to some degree, in the form of a film, on virtually all dental surfaces. It is a byproduct of microbial growth, and comprises a dense microbial layer consisting of a mass of microorganisms embedded in a polysaccharide matrix. Plaque itself adheres firmly to dental surfaces and is removed only with difficulty even through a rigorous brushing regimen. Moreover, plaque rapidly reforms on the tooth surface after it is removed. Plaque may form on any part of the tooth surface, and is found particularly at the gingival margin, in cracks in the enamel, and on the surface of dental calculus. The problem associated with the formation of plaque on the teeth lies in the tendency of plaque to build up and eventually produce gingivitis, periodontitis and other types of periodontal disease, as well as dental caries and dental calculus.

Plaque formation is an ongoing process. Although various oral care products are available to control plaque formation such as toothpastes and mouth rinse, the disadvantage of these products is that only a relatively short time during which the teeth are being brushed or the mouth is being rinsed is available for these preparations to take effect. A further disadvantage of these toothpaste and mouth rinse products is the general infrequency of use, that is, most dental hygiene products are used once or perhaps twice daily and seldom when they are most needed, e.g., after meals and snacks. Thus food deposits which build up as a result of eating throughout the day are left in the oral cavity for long periods of time thereby promoting microbial growth and formation of plaque on tooth surfaces.

It is known to the art to incorporate antimicrobial agents in oral compositions wherein these agents destroy or inhibit oral bacteria responsible for plaque formation. Other agents are also incorporated in the oral composition to reduce plaque formation on teeth. For example, it is known to incorporate enzymes such as proteases and carbohydrases in oral compositions, which enzymes disrupt or interfere with plaque formation and bacterial adhesion to tooth surfaces.

Chewable tablets and gums have been used as vehicles for introducing various chemical agents to tooth surfaces including enzymes such as amylase enzymes (U.S. Pat. No. 4,740,368) oxidoreductases such as glucose oxidase and lactoperoxidase enzymes (U.S. Pat. No. 4,564,519).

A critical requirement, however, for these compositions is that they are stable and have a long shelf-life, which requirement has limited the use of these compositions because normally, the active agents incorporated in these compositions that provide oral care benefits such as plaque reduction are not stable under ambient conditions of humidity and temperature and as a result the agents quickly become degraded to concentrations of limited efficacy and particularly, enzymes which denature during the manufacturing process.

In view of the inconvenience of using toothpaste and mouth rinse products when away from home, the art is seeking portable products in the form of chewable confections such as tablets and gums which can be used throughout the day, particularly after eating, and which provide antiplaque benefits comparable to those obtained by regular brushing with a toothpaste or use of a mouthrinse.

SUMMARY OF THE INVENTION

In accordance with the present invention, there is provided a chewable confectionery composition such as a chewable tablet or gum comprised of a small but effective amount of a plaque reducing enzyme, a non-cariogenic sweetener and optionally a plasticizing/softening agent.

Due to the inherent nature of the chewable tablet or gum product, prolonged contact with the tooth surfaces is achieved when the product is chewed, forming a paste with saliva containing the enzyme which coats the tooth surfaces. The delivery of the enzyme in a chewable tablet or gum form insures that an adequate dosage of the antiplaque enzyme is deliverable when the product is chewed by the user. The chewable confectionery composition of the present invention is portable and can be packaged and stored in a consumers pocket or purse for consumption anytime and anywhere.

When the chewable confectionery composition of the present invention is placed within the mouth and chewed, an effective antiplaque amount of the enzyme is released from the composition into the saliva where it can reach the surface of the teeth to prevent further plaque accumulation. The tablet or gum of the present invention is formed so as to release the enzyme over a period of 0.5 to 2 minutes. Consistent daily use of the chewable tablets or gums of the present invention will then obtain maximum plaque reduction from the teeth of the consumer.

The term "chewable confectionery composition" as used herein includes within its meaning chewing gum, and chewable and orally soluble tablets, troches and lozenges.

DESCRIPTION OF THE PREFERRED EMBODIMENTS

The composition of the present invention as stated is a chewable product which reduces plaque and contains as the active ingredient, a protease enzyme. The product is preferably sugarless.

A representative chewable antiplaque tablet in accordance with the practice of this invention contains about 0.1 to 3% by weight of an enzyme, 0.5 to 5% by weight of a combination plasticizing/softening ingredient and about 50 to about 90% by weight of a non-cariogenic sweetener. In addition to the ingredients discussed above for tablets, chewable gum compositions will contain 10 to 40% by weight of a gum base.

As water promotes the denaturization of the papain enzyme, the presence of water in the chewable confectionery product of the present invention should be at relatively low concentrations in order to impart maximum stability and shelf life to the chewable. For this purpose, it has been found essential to limit the total amount of water present in the chewable product to no more than 5% by weight.

Enzymes

The enzymes useful in the practice of the present invention include carbohydrases such as glucoamylase and enzymes extracted from natural fruit products such as proteases which breakdown or hydrolyze proteins.

Protease enzymes useful in the practice of the present invention include those extracted from natural fruit products. The proteolytic enzymes are obtained from natural sources or by the action of microorganisms having a nitrogen source and a carbon source. Examples of proteolylic enzymes useful in the practice of the present invention include the naturally occurring enzymes papain (from papaya), bromelain (from pineapple), as well as serine proteases such as chymotrypsin. Additional enzymes include ficin and alcalase. Papain is a protease enzyme preferred for use in the practice of the present invention, the papain having an activity of 150 to 939 MCU per milligram as determined by the Milk Clot Assay Test of the Biddle Sawyer Group (see J. Biol. Chem., vol. 121, pages 737-745). The protease enzymes are included in the compositions of the present invention at a concentration of about 0.1 to about 3% by weight and preferably about 0.2 to about 2% by weight.

Enzymes which may beneficially be used in combination with the proteolytic enzymes and glucoamylase enzymes include carbohydrases such as glucoamylase, alpha-amylase, beta-amylase, tannase and lipases such as plant lipase, gastric lipase and pancreatic lipase.

Glucoamylase is a saccharifying glucoamylase of Aspergiullus niger origin cultivated by fermentation. This enzyme can hydrolyze both the alpha-D-1,6 glucosidic branch points and the alpha-1,4 glucosidic bonds of glucosyl oligosaccharides. Additional carbohydrases useful in accordance with this invention are alpha and beta-amylase, dextranase and mutanase. Glucoamylase is a preferred enzyme and is incorporated in the oral composition of the present invention at a concentration of about 0.001 to 2% by weight and preferably about 0.01 to 0.55% by weight.

The lipase enzyme is derived from a select strain of *Aspergillus niger*, exhibiting random cleaving of the 1,3 positions of fats and oils. The enzyme has maximum lipolytic activity at pH 5.0 to 7.0 when assayed with olive oil. The enzyme has a measured activity of 120,000 lipase units per gram. The lipase may be included in the dentifrice composition at a concentration of about 0.010 to about 5.0% by weight and preferably about 0.02 to about 0.10% by weight.

The presence of tannase enzyme can be further beneficial in facilitating the breakdown of extrinsic stain. Tannase enzymes have been purified from *Aspergillus niger* and *Aspergillus allianceus* and are useful in the hydrolysis of tannins, known to discolor the tooth surface.

Other suitable enzymes which can comprise the present invention include lysozyme, derived from egg white, which contains a single polypeptide chain crosslinked by four disulfide bonds having a molecular weight of 14,600 daltons. The enzyme can exhibit antibacterial properties by facilitating the hydrolysis of bacterial cell walls cleaving the glycosidic bond between carbon number 1 of N-acetylmuramic acid and carbon number 4 of N-acetyl-D-glucosamine, which in vivo, these two corbohydrates are polymerized to form the cell wall polysaccharide. Additionally, pectinase, an enzyme that is present in most plants facilitates the hydrolysis of the polysaccharide pectin into sugars and galacturonic acid. Finally, glucanase, which may be utilized to catalyze the breakdown of complex carbohydrates to glucans and the hydrolysis of beta glucan to glucose.

Enzyme Stabilizing Agents

Enzyme stabilizing agents which protect the enzyme from inactivation by chelating metal impurities present in the chewable confectionery composition of the present invention may be incorporated in the composition include ethylene diamine tetraacetic acid (EDTA) and sodium gluconate at concentrations between 0.01 and 1% by weight, preferably between 0.1 and 0.5% by weight. Agents stabilizing the enzyme against oxidation include reducing agents such as sodium bisulfite, metal gallates, potassium stannate, sodium stannate, ammonium sulfate, 3,5,-di-tert-butyl-4-hydroxytoluene (BHT), Vitamin E ($\alpha$, $\beta$,$\gamma$, forms)/Vitamin E acetate and ascorbic acid. Potassium stannate is an enzyme stabilizing agent preferred for use in the practice of the present invention. The reducing agent is present in the oral composition of the present invention at a concentration between about 0.05 to about 1.5% by weight, preferably between about 0.1 and about 0.75% by weight.

Tablets

Plasticizing/Softening Agents

Plasticizing/softening agents suitable for use in the preparation of tablets in accordance with the practice of this invention, include propylene glycol, glycerol, acetylated monoglyceride, glyceryl triacetate, glyceryl diacetate, lecithin, glycerin, and mixtures thereof. In a preferred embodiment of this invention, a combination of lecithin and glycerin is used, generally in amounts of about 0.5% to about 3.0% by weight, 0.1% to about 1.0% lecithin and about 1.0% to about 1.0% by weight glycerin by weight, based on the weight of the total chewable tablet composition.

Sweeteners

The sweetening agent ingredient used in the practice of the present invention include bulk sweeteners such as the polyols of 5 to 12 carbon atoms substituted with 5 to 9 hydroxyl groups such as sugar alcohols including xylitol, sorbitol, mannitol. Sugar alcohols provide bulk or texture to the chewable compositions of the present invention and are utilized in amounts of about 25% to about 90% by weight preferably about 40% to about 85% by weight Artificial sweeteners include as sodium or calcium saccharin salts, cyclamate salts, such as the sodium salt and the like, and the free acid form of saccharin; dipeptide based sweetening agents such as L-aspartyl-L-phenyl-alanine methyl ester, dihydrochalcone; glycyrrhizin; and the synthetic sweetener 3,6-dihydro-6-methyl-1, 1,2,3-oxathiazin-4-one-2,2-dioxide, particularly the potassium (Acesulfame-K), sodium and calcium salts. Artificial sweeteners are present in the chewable confectionery compositions of the present invention at a concentration of about 0.1 to about 1% by weight.

Preferred bulk sweeteners include Lycasin, a commercially available mixture of sorbitol, malitol and high molecular weight dextrans disclosed in Re 26,969 and Isomalt, a sugar alcohol of a disaccharide such as alpha-D-glucopyranosyl-1, 6-mannitol, its isomer, alpha, D-glucopyranosyl-1, 6-sorbitol or a mixture thereof which is obtained by the hydrogenation of palatinose which is converted from sucrose as a raw material with glycosyltransferase. A preferred artificial sweetener is aspartame.

In a preferred embodiment of this invention, the sweetening agent used is a combination of an artificial sweetener such as aspartame and acesulfame and the bulk sweeteners such as Lycasin and Isomalt, the artificial sweetener being present generally in amounts of about 0.05% to about 0.3% by weight and preferably about 0.18% to about 0.22% by weight and about 40% to about 60% by weight, preferably about 45% to about 55% by weight Lycasin and about 15% to about 35% by weight preferably about 20% to about 30% by weight Isomalt.

Flavoring Agents

One or more flavoring agents in liquid powder or encapsulated form are used in the chewable composition of this invention. A variety of flavors known in the art may be used, including essential oils, such as cinnamon, spearmint, peppermint, menthol, birch, anise wintergreen oil and eucalyptus oil. Natural fruit flavors derived from the essence of fruits, such as apple, pear, peach, strawberry, cherry, apricot, orange, watermelon, banana and the like; bean derived flavors such as coffee, cocoa and the like; wine derived curacao zin and the like, and pungent materials, such as affinin, pepper, mustard and the like. Flavoring agents are incorporated in the chewable confectionery compositions at a concentration of about 0.5 to about 5% by weight and preferably about 1.0 to about 3.0% by weight.

Other Ingredients

Calcium salts may be incorporated in the chewable compositions of the resent invention as fillers and anticavity agents. Examples of the calcium salts to be used in the present invention as the anticaries agent are, for example, calcium chloride, calcium nitrate, calcium sulfate, dicalcium phosphate dihydrate, calcium carbonate, calcium citrate, calcium hydrogen pyrophosphate, calcium gluconate, calcium glycerophosphate, calcium hydroxide, calcium oxide, calcium silicate and the like, but not limited thereto. The calcium salt is present in the tablet or gum at a concentration of about 5 to about 20% by weight and preferably 7 to 10% by weight. Alkaline agents such as sodium bicarbonate may be incorporated in the chewable confectionery composition of the present invention to provide additional cleaning and breath freshening properties to the composition.

Chewing Gum

The chewing gum of the present invention is preferably a sugarless chewing gum containing the enzyme, as sugarless gums do not promote tooth decay. Chewing gum formulations in which the enzymes of the present invention may be incorporated are well known in the art and typically contain, in addition to, a chewing gum base, one or more plasticizing agents; at least one sweetening agent and at least one flavoring agent.

Gum base materials suitable for use in the practice of this invention are well known in the art and include natural or synthetic gum bases or mixtures thereof. Representative natural gums or elastomers include chicle, natural rubber, jelutong, balata, guttapercha, lechi caspi, sorva, guttakay, crown gum, perillo, or mixtures thereof. Representative synthetic gums or elastomers include butadiene-styrene copolymers, polyisobutylene and isobutylene-isoprene copolymers.

The gum base is incorporated in the chewing gum product at a concentration of about 10 to about 40% by weight and preferably about 20 to about 35% by weight.

Plasticizing/softening agents commonly used in chewing gum compositions are suitable for use in this invention, including gelatin, waxes and mixtures thereof in amounts of 0.1 to 5% by weight.

The sweetening agent ingredient used in the practice of this invention may be selected from a wide range of materials. Bulk sweeteners include the same sweeteners used for the preparation of chewable tablets as are artificial sweeteners. The bulk sweetener is present in the chewing gum composition of the present invention in amounts of about 40 to about 80% by weight and preferably about 50 to about 75% by weight. The artificial sweetener is present in the chewing gum composition of the present invention in amounts of about 0.1 to about 2% by weight and preferably about 0.3 to 1% by weight.

In addition to the ingredients listed above, the gum compositions may also include conventional additives such as colorants, flavoring agents and the like. For example, titanium dioxide may be utilized as a colorant. A variety of flavors known in the art may be used, including essential oils, such as cinnamon, spearmint, peppermint, menthol, birch, anise and the like; natural fruit flavors derived from the essence of fruits, such as apple, pear, peach, strawberry, cherry, apricot, orange, watermelon, banana and the like; bean-derived flavors, such as coffee, cocoa and the like. Flavoring agents are incorporated in the chewing gum formulation at a concentration of about 0.5 to about 5% by weight and preferably 1 to 3% by weight.

Method of Manufacture

The challenge in incorporating enzymes into the confectionary composition is maintaining enzymatic stability and activity during storage. Enzymes are quaternary proteins whose structure, function, and stability are sensitive to chemical environment and processing parameters. Enzymes denature in harsh chemical environment and at high temperatures. Formulation and processing procedures are optimized at low moisture and low temperature for both the enzyme chewable tablet and the enzyme gum to preserve enzymatic activity and in vivo efficacy.

The chewable composition of the present invention is made by any suitable process where the protease enzyme is incorporated into the solid base material such that no water or a limited amount of ingredients that absorb water are used that would result in undesirable amounts of water being introduced into the composition during processing or storage. Further, at the time the enzyme is introduced into ingredients used to prepare the chewable composition that the temperature at the time of addition is less then about 80° C. Therefore, it is critical to the practice of the present invention that the composition contain less than 5% by weight water and preferably less than 3% by weight water and that the temperature at which processing of the enzyme occurs be less than about 80° C. The presence in the composition of water in amounts greater than 5% by weight or the use of temperatures in excess of 80° C. will act to denature the protease enzyme thereby substantially reducing the efficacy of the enzyme in effecting plaque reduction on teeth.

One method for manufacturing the composition of the invention comprises first heating the base material to a temperature sufficient to drive off any water in the composition. The base material is then cooled to a temperature at which the enzyme and other temperature sensitive ingredients such as plasticizers, other sweeteners are incorporated and mixed into the base material.

Formulations, equipment and processing techniques have been well developed in the art for preparing and packaging chewing gum and chewable tablets and lozenges. As the enzyme is subject to deterioration and inactivation under conditions such as high shear and elevated temperatures, processing conditions are controlled during the time period that the enzymes are admixed with the other ingredients of the formulation and converted into finished products so that the temperature at the time of admixture does not exceed about 80° C. for any extended period of time.

The tablets of the confectionary composition of the present invention are conventionally made by grinding the ingredients once mixed and then compressing or molding the ingredients to form a suitable means for the delivery of the enzyme. In order to produce tablets it is necessary to have a free flowing material which has good self binding properties and which will not stick to the molding or compression equipment.

An illustrative procedure for formulating the chewing gum composition is as follows: the gum base is first melted in a heated kettle at 55'-65° C. One or more of the sweeteners are then added to the gum base followed by one or more flavors, plasticizer. All ingredients are then mixed for a sufficient period of time to ensure adequate dispersion. The mixture is then allowed to cool and the enzyme is added and is cut into suitable serving sizes.

In order to enhance shelf stability, in addition to the admixture used in the preparation of the chewable product being substantially free of water, the finished product should be packaged in a manner so as to minimize exposure to air and moisture.

The following Examples are illustrative of the present invention, but it is understood that the invention is not limited thereto.

EXAMPLE I

Enzyme (papain) containing tablet and gum compositions were prepared using conventional base ingredients as set forth in Tables I and II below.

TABLE I

| CHEWABLE TABLET | |
| --- | --- |
| Ingredient | Wt. % |
| Papain | 0.5 |
| Lycasin 75% | 48.9 |
| Isomalt | 23.1 |
| Hydrogenated vegetable oil | 8.7 |
| Water | 4.8 |
| Gelatin (40% solution) | 2.9 |
| Starch coated dicalcium phosphate | 8.7 |
| Mono-diglyceride mixture | 0.8 |
| Lecithin | 0.3 |
| Aspartame | 0.05 |
| Aspartame K | 0.05 |
| Vanillin | 0.05 |
| Glycerin | 0.1 |
| Sodium bicarbonate | 0.10 |
| Mint flavor | 0.19 |

The chewable tablet of Table I was prepared by boiling the Isomalt, Lycasin, water, fat, mono and diglyceride mixture, glycerin, and lecithin to 267-268° F. (131° C.) after which glycerin was added and the mixture and cooled to 140° F. (60° C.). Thereafter sodium bicarbonate, papain, dicalcium phosphate and the remaining ingredients were added. Thereafter the mixture cooled to room temperature 72-77° F. (23° C.) was ground into powder and compressed into a tablet using a tablet press.

TABLE II

| CHEWING GUM | |
| --- | --- |
| Ingredient | Wt. % |
| Gum base | 31.20 |
| Sorbitol | 28.08 |

TABLE II-continued

| CHEWING GUM | |
| --- | --- |
| Ingredient | Wt. % |
| Mannitol | 5.23 |
| Papain | 1.00 |
| Acesulfame K | 0.16 |
| Aspartame | 0.16 |
| Menthol powder | 1.00 |
| Liquid flavor | 0.47 |
| Isomalt PF | 11.70 |
| Isomalt DC | 16.00 |
| Anticaking agents* | 4.00 |
| Flavor | 2.00 |

*Magnesium stearate, talc, silica gel.

Papain Enzyme Activity

Papain activity was measured and monitored in the papain containing chewable tablets and chewing gums using the Protease Detection kit from Panvera Corp. The activity kit quantifies protease activity using a fluorenscein thiocarbamoyl (FTC)-casein substrate. FTC-casein is attacked by the protease, breaking down casein into TC-peptides. The amount of protease activity is determined by measuring the fluorescence expressed as relative fluorescence units (RFU). The fluorescence signal generated is proportioned to the level of activity of papain in the tablet or gum delivery system. For the purposes of comparison, chewable tablets designated "Tablet A" and chewing gum designated "Chewing Gum B" were prepared in which papain was not included in these compositions. The papain activities of the chewable tablet or Table I and the chewing gum of Table II are recorded in Tables III and IV below as are the papain activities of comparative tablet and gum compositions.

TABLE III

| Protease Activity Chewable Tablet Fluorescence | | |
| --- | --- | --- |
| Composition | 4 Weeks (RFU) | 8 Weeks (RFU) |
| Table I | 29,000 | 30,000 |
| A | 2,000 | 2,000 |

TABLE IV

| Chewing Gum Fluorescence | |
| --- | --- |
| Composition | 4 Weeks (RFU) |
| Table II | 38,000 |
| B | 1,500 |

The results recorded in Tables III and IV indicate that the enzyme activity in papain when incorporated in a chewable tablet or gum is retained over at least a 4 week period.

In Vivo Plaque Reduction Efficacy

The chewable tablet of Table I was tested for plaque reduction at 2-and 5-hours after chewing by human volunteers using plaque grown in vivo in an intra-oral retainer on hydroxyapatite disks. Confocal microscopy was used to visualize and quantify the changes in plaque coverage and plaque ultrastructure. Plaque removal was also measured by conventional light microscopy by staining the plaque before and after treatment with crystal violet indicator and measuring the changes in color intensity. Image Pro Analysis Software was used to perform the image analysis and the quantitative measurements. The color intensity was measured and used to determine stain removal. The greater the intensity, the greater the cleaning efficacy. These results are shown in Table V below.

TABLE V

Chewable Tablet Plaque Reduction Efficacy

| | Total Area (Microns^2) | % Reduction from Baseline | Average Cluster Area (Microns^2) | % Reduction |
|---|---|---|---|---|
| Baseline | 8681 | — | 54.45 | — |
| 2 hours | 3537 | 59 | 20.10 | 63 |
| 5 hours | 2959 | 66 | 26.18 | 52 |

Confocal images were made of the plaque before treatment (baseline) and 2 and 5 hours after treating with the tablet. Qualitatively, images showed that there is less bacterial coverage 2 and 5 hours after treatment in comparison to baseline. Image analysis was used to quantify these observations. The results recorded in Table V indicated that the total plaque area, measured by pixel counting, was significantly reduced in comparison to baseline and 2 and 5 hours after treatment. Table V also shows that the average cluster area of the plaque bacteria was significantly reduced after treatment demonstrating the significant efficacy in reducing plaque without the aid of mechanical assistance.

In a second study, the plaque before and after staining with crystal violet was viewed by conventional light microscopy. Image analysis was used to determine the white intensity measured in pixels, the higher the pixel number, the whiter the stain. The results from this study are shown in Table VI. The disks stained at baseline were more intensely colored (blue) than the disks stained 2 hours after treatment with the papain containing chewable tablet. The disks were 47.3% whiter than baseline, indicating less staining and therefore, less plaque. Similar results were observed with the papain chewing gum of Table II as shown in Table VII below.

TABLE VI

Chewable Tablet Staining Removal (White Intensity)

| | | | | Average | Improvement from Baseline |
|---|---|---|---|---|---|
| Baseline | 125 | 100 | — | 112.5 | — |
| Treatment | 240 | 200 | 200 | 213.3 | 47.3% |

TABLE VII

Chewing Gum Plaque Reduction Efficacy

| | Total Area (Microns^2) | % Reduction from Baseline | Average Cluster Area (Microns^2) | % Reduction |
|---|---|---|---|---|
| Baseline | 47,832 | — | 2897 | — |
| 2 hours | 38,137 | 16 | 2446 | 15 |
| 5 hours | 27,267 | 52 | 1398 | 52 |

What is claimed is:

1. A chewable confectionery composition comprising:
   a) an enzyme comprising a protease which has been extracted from a fruit and wherein said enzyme is incorporated into a gum base;
   b) a non-cariogenic sweetener; and
   c) an enzyme stabilizing agent which is a metal chelating agent or an antioxidation agent;
   wherein the composition contains less than 5% by weight water the enzyme is incorporated into the composition at a temperature of less than 80° C.; and the enzyme maintains its initial activity over at least a 4 week period when stored at 23° C.

2. The composition of claim 1, wherein the enzyme is papain or bromelain and is present at a concentration of about 0.1 to 3% by weight.

3. The composition of claim 2, wherein the enzyme is present at a concentration of about 0.2 to about 2% by weight.

4. The composition of claim 1, wherein the enzyme is papain.

5. The composition of claim 1, wherein the non-cariogenic sweetener is a sugar alcohol or an artificial sweetener.

6. The composition of claim 1, wherein the non-cariogenic sweetener is a polyol of 5 to 12 carbon atoms substituted with 5 to 9 hydroxyl groups.

7. The composition of claim 5 wherein the sugar alcohol is xylitol, sorbitol, or mannitol.

8. The composition of claim 1, wherein the non-cariogenic sweetener is a sugar alcohol present at a concentration of about 25% to about 95% by weight.

9. The composition of claim 8, wherein the sugar alcohol is present at a concentration of about 40% to about 85% by weight.

10. The composition of claim 8, wherein the sugar alcohol is a sugar alcohol of a disaccharide.

11. The composition of claim 1, wherein the non-cariogenic sweetener is an artificial sweetener and is present at a concentration of about 0.1 to about 1% by weight.

12. The composition of claim 11, wherein the artificial sweetener is a sodium or calcium saccharin salt, a cyclamate salt, the free acid form of saccharin; a dipeptide sweetening agent, 3,6-dihydro-6-methyl-1, or 1,2,3-oxathiazin-4-one-2,2-dioxide.

13. The composition of claim 1 which is a chewing gum, or a chewable and orally soluble tablet, troche, or lozenge.

14. The composition of claim 13 which is a tablet.

15. The composition of claim 13 which is a chewing gum and comprises a gum base at a concentration of about 10 to about 40% by weight.

16. The composition of claim 15 which comprises a gum base at a concentration of about 20 to about 35% by weight.

17. The composition of claim 15, wherein the gum base is chicle, natural rubber, jelutong, balata, guttapercha, lechi caspi, sorva, guttakay, crown gum, perillo, butadiene-styrene copolymers, polyisobutvlene, or isobutylene-isoprene copolymers, or mixtures thereof.

18. The composition of claim 1, wherein the metal chelating agent is ethylene diamine tetraacetic acid or sodium gluconate and is present at a concentration between 0.01% and 1% by weight.

19. The composition of claim 18, wherein the metal chelating agent is present at a concentration between 0.1 and 0.5% by weight.

20. The composition of claim 1, wherein the antioxidation agent is sodium bisulfite, a metal gallate, potassium stannate, sodium stannate, ammonium sulfate, 3,5,-di-tert-butyl-4-hydroxytoluene, or vitamin E.

21. The composition of claim 20, wherein the antioxidation agent is potassium stannate.

22. The composition of claim 20, wherein the antioxidation agent is present at a concentration between about 0.05 to about 1.5% by weight.

23. The composition of claim 22, wherein the antioxidation agent is present at a concentration between about 0.1 and about 0.75% by weight.

24. The composition of claim 1 further comprising a plasticizing/softening agent which is gelatin, wax, propylene glycol, glycerol, acetylated monoglyceride, glyceryl triacetate, glyceryl diacetate, lecithin, or glycerin, and mixtures thereof.

25. The composition of claim 24, comprising a combination of lecithin and glycerin in amounts of about 0.5% to about 3.0% by weight lecithin and about 0.1 to about 1.0% by weight glycerin.

26. The composition of claim 1 further comprising calcium salts at a concentration of about 5 to about 20% by weight.

27. The composition of claim 26, wherein the salt is calcium chloride, calcium nitrate, calcium sulfate, dicalciam phosphate dihydrate, calcium carbonate, calcium citrate, calcium hydrogen pyrophosphate, calcium gluconate, calcium glycerophosphate, calcium hydroxide, calcium oxide, or calcium silicate.

28. The composition of claim 1 comprising about 0.1 to 3% by weight of an enzyme, 0.5 to 5% by weight of a combination plasticizing/softening ingredient, and about 50 to about 90% by weight of a non-cariogenic sweetener, and 10 to 40% by weight of a gum base.

* * * * *